(12) United States Patent
Vaska et al.

(10) Patent No.: US 8,387,620 B1
(45) Date of Patent: Mar. 5, 2013

(54) ORAL DEVICE FOR ANTERIOR ADVANCEMENT AND MEDIAL CONSTRAINT OF THE TONGUE

(75) Inventors: Matthias Vaska, Palo Alto, CA (US); Jonathan L. Podmore, San Carlos, CA (US); Nicholas R. Vitale, Foster City, CA (US); Michael C. Hozbaur, Menlo Park, CA (US); John Edwards Crowe, Menlo Park, CA (US); Sean Christopher Daniel, Palo Alto, CA (US)

(73) Assignee: Apnicure, Inc., Redwood City, CA (US)

( * ) Notice: Subject to any disclaimer, the term of this patent is extended or adjusted under 35 U.S.C. 154(b) by 0 days.

(21) Appl. No.: 13/593,137

(22) Filed: Aug. 23, 2012

(51) Int. Cl.
*A61F 5/56* (2006.01)
*A61C 5/14* (2006.01)

(52) U.S. Cl. .......... 128/848; 128/859; 128/860

(58) Field of Classification Search .......... 128/848, 128/859–862, 200.24, 207.14, 207.15; 433/6–7
See application file for complete search history.

(56) References Cited

U.S. PATENT DOCUMENTS

| | | | |
|---|---|---|---|
| 6,494,209 B2 | 12/2002 | Kulick | |
| 6,595,209 B1 | 7/2003 | Rose et al. | |
| 7,328,698 B2 * | 2/2008 | Scarberry et al. | 128/200.24 |
| 8,074,656 B2 | 12/2011 | Vaska et al. | |
| 8,122,889 B2 | 2/2012 | Vaska et al. | |
| 8,122,890 B2 | 2/2012 | Vaska | |
| 2005/0166928 A1 | 8/2005 | Jiang | |
| 2005/0166929 A1 | 8/2005 | Jiang | |
| 2007/0277818 A1 | 12/2007 | Chen | |
| 2009/0120446 A1 | 5/2009 | Vaska et al. | |
| 2009/0120447 A1 | 5/2009 | Vaska et al. | |
| 2009/0123886 A1 | 5/2009 | Vaska | |
| 2011/0220124 A1 | 9/2011 | Vaska et al. | |
| 2011/0259346 A1 | 10/2011 | Tsuiki et al. | |
| 2012/0017917 A1 | 1/2012 | Podmore et al. | |
| 2012/0037166 A1 | 2/2012 | Podmore et al. | |
| 2012/0132215 A1 | 5/2012 | Vaska et al. | |
| 2012/0132216 A1 | 5/2012 | Vaska | |
| 2012/0199135 A1 | 8/2012 | Podmore et al. | |

OTHER PUBLICATIONS

U.S. Appl. No. 13/476,855, filed May 21, 2012, Podmore et al.
U.S. Appl. No. 13/546,453, filed Jul. 11, 2012, Vitale et al.
Tsuiki, et al. Tongue position controller as an alternative treatment for obstructive sleep apnea. American Journal of Respiratory and Critical Care Medicine 2012; 185:A6461.

* cited by examiner

*Primary Examiner* — Patricia Bianco
*Assistant Examiner* — Ophelia A Hawthorne
(74) *Attorney, Agent, or Firm* — Wilson, Sonsini, Goodrich & Rosati (57) ABSTRACT

An oral device for temporary placement in a patient's oral cavity includes a base, a tongue-engaging member and a tongue pocket. Partial vacuums are separately drawn through the tongue-engaging member and the tongue pocket in order to advance and control the position of the tongue in order to clear the patient's airway to reduce sleep apnea or treat other conditions.

28 Claims, 4 Drawing Sheets

ORAL DEVICE FOR ANTERIOR ADVANCEMENT AND MEDIAL CONSTRAINT OF THE TONGUE

BACKGROUND OF THE INVENTION

1. Field of the Invention

The present invention relates generally to medical devices and methods. In particular, the present invention relates to an oral device that may be held in the mouth of a patient to reduce the incidence of obstructive sleep apnea or snoring.

Obstructive sleep apnea (OSA) is a serious medical condition resulting from a temporary airway blockage which occurs as a patient sleeps. The airway blockage usually occurs between the soft palate and/or the back of the tongue and the pharynx. As the patient breathes, the reduced area in the upper airway can cause snoring, and more seriously, OSA. Sleep disruption caused by OSA can result in severe daytime sleepiness, chronic fatigue, headaches, depression, accidents, injuries, and of particular concern, OSA can reduce the amount of oxygen entering the lungs causing hypoxia. Hypoxia, in turn, can lead to pulmonary hypertension, heart disease, and stroke.

Numerous invasive and less invasive treatments have been proposed for OSA. Of particular interest to the present invention, "continuous positive airway pressure" (CPAP) delivers a continuous stream of pressurized air directly to the person's upper airway. The positive pressure maintains patency of the airway and inhibits the collapse associated with OSA. Although generally effective, CPAP suffers from a number of drawbacks that have led to a high level of non-compliance. The patient must wear a bulky facial mask which can be uncomfortable, and the system generates noise that can make falling asleep difficult. CPAP is also difficult to use because the mask requires careful fitting to avoid air leaks and facial discomfort and because the mask can easily be dislodged during sleep. Moreover, a number of unpleasant side effects, such as sore throats, dry throat and eyes, headaches, and skin rashes from the mask frequently occur. These problems have resulted in a high level of non-compliance with CPAP therapy.

As an improvement over CPAP, it has been proposed to apply a negative pressure to the forward end of the patient's mouth, typically at or just behind the lips, to pull the tongue forward in order to lift the rear portion of the tongue away from the back of the airway. See, for example, U.S. Pat. Nos. 6,494,209 and 7,328,698, and U.S. Patent Publication Nos. 2011/0259346; 2007/0277818; 2005/0166928 and 2005/0166929. While promising in theory, in practice it is very difficult to apply a vacuum in the region of the tip of the tongue to raise the base of the tongue and clear the patient's airway, particularly when the patient is lying on his or her back and gravity is pulling the tongue posteriorly. The tongue is a relatively large and compliant organ with significant mass, and applying a vacuum over a relatively small surface area at the tip will often not be effective in raising the back of the tongue against gravity. The moist and compliant tissues in the mouth are somewhat self-sealing, and this effect tends to inhibit the propagation of negative pressure, thereby confining the negative pressures to a relatively small area near the point of application. Thus, simply applying a vacuum at a location near the anterior tip of the tongue tends to draw the tongue up against the hard palate posterior to this location, creating a seal that restricts the propagation of vacuum through this region of contact toward the back of the oral cavity, where direct vacuum is usually required for maximum effectiveness.

As another improvement over CPAP, it has been proposed to place various devices in direct contact with the posterior tissues of the mouth such as the soft palate and posterior portions of the tongue. A major disadvantage of these approaches is that contact with certain tissues near the posterior area of the tongue may elicit the gag reflex and in any case the presence of such devices so far back in the mouth can be uncomfortable.

Still further improvements in the treatment of sleep apnea are described in U.S. Pat. Nos. 8,074,656; 8,074,656; and 8,122,889, and U.S. Patent Publication 2012/0017917, assigned to the assignee of the present application, the full disclosures of which are incorporated herein by reference. These patents describe engaging a lateral element across a medial region of the tongue to create a clearance above the tongue. By drawing a vacuum in the clearance, the soft palate can be drawn forward to open the airway. While very successful in many patients, the treatment is not fully effective in some patients.

For these reasons, it would be desirable to provide alternative and improved methods and apparatus for treating obstructive sleep apnea and snoring. The methods and devices should be non-invasive and require no surgery or permanently implanted components. In addition, the methods and devices should be minimally intrusive with components that are comfortable and quiet so that disruption of the patient's sleep is minimized. Moreover, the methods and devices should avoid contacting the portions of the oral cavity that trigger the gag reflex. The methods and systems should also be simple to implement and be effective to significantly improve patency of a patient's airway during sleep in a broad population of patients suffering from sleep apnea. At least some of these objectives will be met by the inventions described hereinafter.

2. Description of the Background Art

U.S. Pat. Nos. 8,074,656; 8,122,889; and 8,122,890, and U.S. Patent Publication Nos. 2012/007917 and 2012/0199135, assigned to the assignee of the present application, describe oral appliances for engaging a medial region of a patient's tongue to maintain airway patency. U.S. Pat. Nos. 6,595,209 and 7,328,698, and U.S. Patent Publication No. 2011/0259345, oral appliances for applying a vacuum to pull an anterior region of a patient's tongue forward to treat sleep apnea. See also Tsuiki et al. (2012) AM. J. Respir. Crit. Care Med. 185: A6461.

SUMMARY OF THE INVENTION

The present invention provides devices and methods for improving airway patency by simultaneously advancing an anterior region of a patient's tongue and constraining or depressing a medial region of the tongue while applying a first partial vacuum in a space created over the tongue by the constraint. In this way, both the tongue and the soft palate can be brought forward to clear the airway more reliably and for a greater number of patients than either action can consistently achieve by itself. In specific embodiments of the present invention, the tongue is brought forward by applying a second partial vacuum to an anterior region of the tongue, where the vacuum applied above the tongue and the vacuum applied to the anterior region of the tongue will usually be separately controlled and will usually be applied at different levels so that the patient and/or physician can separately adjust the levels of vacuum applied to the tongue and to the soft palate to optimize treatment for each individual patient.

In a first aspect of the present invention, an oral device is adapted for temporary placement in a patient's oral cavity.

The oral device comprises a base, a tongue-engaging member, and a tongue pocket. The base is adapted to be held between the patient's upper and lower teeth, where the base has an anterior opening which is adapted to allow the patient's tongue to pass therethrough. The tongue-engaging member is coupled to the base, typically at a posterior end thereof, and is disposed to engage a medial region of the tongue when the base is positioned between the patient's teeth. The tongue pocket is usually coupled to the base and has an interior disposed to receive the anterior region of the patient's tongue when the tongue passes through the anterior opening in the base.

The tongue pocket is adapted to be connected directly or indirectly to a vacuum source to apply a partial vacuum within the pocket to draw the tongue forward when the tongue is present through the anterior opening. The tongue-engaging member of the oral device may also be connected to a vacuum source, and in some instances a single vacuum source may be used for both the tongue pocket and the tongue-engaging members. For example, the oral device may include passages and structure which allow a partial vacuum to be drawn in a region within the oral cavity disposed above the medial region of the tongue when the tongue-engaging member is engaged against the tongue. In such embodiments, the partial vacuum in the oral cavity may serve to draw the tongue into the tongue pocket. In other embodiments, as described in more detail below, the tongue pocket and tongue-engaging member each may have separate passages and structures for connection to separate vacuum sources for drawing vacuums within the tongue pocket and the patient's oral cavity, thus allowing different vacuum levels to be drawn in the pocket and in the oral cavity.

In specific embodiments of the devices of the present invention, the tongue/engaging member is adapted to be connected to a vacuum source to apply a partial vacuum in the oral cavity to draw the patient's soft palate toward a posterior surface of the tongue-engaging member. In other embodiments, a separate device or structure may be provided for drawing a vacuum in the region of the tongue-engaging member.

Both the tongue pocket and the tongue-engaging member will typically be provided with a single vacuum source, but alternatively they may be provided with separate vacuum sources which are separately connectable to the member and pocket, respectively. The vacuum sources will be separately controllable, and the vacuum source connected to or otherwise associated with the tongue-engaging member will typically be adapted to draw a vacuum in the range from 10 $cmH_2O$ to 75 $cmH_2O$, usually from 25 $cmH_2O$ to 50 $cmH_2O$. The partial vacuum applied by the tongue pocket will typically be higher (more negative), usually being in the range from 25 $cmH_2O$ to 100 $cmH_2O$, typically being in the range of 35 $cmH_2O$ to 55 $cmH_2O$. In further specific embodiments of the present invention, the tongue pocket will be provided with both a vacuum port for connecting to the vacuum source and a bleed port to allow a continuous flow and release of air through the tongue pocket while maintaining a partial vacuum. The resulting continuous flow through the tongue pocket, although often at a very low rate, will help draw moisture from the anterior of the tongue pocket and allow the connecting tubes and lines to be flushed to remove saliva which might otherwise collect.

The oral devices of the present invention will typically also include one or more vacuum sources which are connectable to the tongue pocket and to the tongue-engaging member. Typically, a first vacuum source is connectable to a vacuum port on the tongue pocket while the bleed port is attached to a flow regulator, such as a fixed orifice or variable control valve in order to help limit airflow through the tongue pocket and control the vacuum level within the pocket.

Similarly, a separate vacuum source may be connected to an outlet port of the tongue-engaging member with a flow regulator connected to the bleed port to allow fresh air to enter through the bleed port and to circulate before exiting to help clear moisture. As with the tongue pocket, the vacuum pump and/or the flow regulator will be controlled to maintain a target vacuum level within the oral cavity in the region of the tongue-engaging member. Usually, both vacuum pumps, both air flow regulators, and a programmable controller will be provided within a common housing which is connectable by a tube set to the oral device. In other cases, it might be possible to utilize a single vacuum source and/or a single flow regulator where the components would have at least two channels allowing for separate levels of vacuum to be applied to the tongue pocket and to the tongue-engaging member, respectively, or allow air flow to be separately regulated to each of the tongue pocket and the tissue-engaging member.

The pressures within the tongue pocket and in the region of the oral cavity near the tongue-engaging member will typically be controlled based on pressure and/or flow measurements of the air into and/or out of the tongue pocket and tissue-engaging member. The pressure will usually be controlled by conventional feedback control algorithms, and the vacuum pump will typically be a positive-displacement pump where the amount of air withdrawn (vacuum applied) can be adjusted by changing the speed of the pump. Such control systems are described in copending, commonly owned application Ser. No. 13/023,763, filed Feb. 9, 2011, the full disclosure of which is incorporated herein by reference.

In a second aspect of the present invention, methods for stabilizing a soft palate in patient's oral cavity comprise engaging a member against a medial region of the tongue to provide a clearance over the tongue. A vacuum is applied within the clearance to draw the soft palate toward a posterior region of the tongue. Simultaneously, an anterior region of the tongue is drawn forward in order to help clear the tongue and further open the patient's airway.

In specific embodiments, the anterior region of the tongue is drawn forward by capturing the tongue in a tongue pocket and applying a vacuum in the pocket. In preferred embodiments, the vacuum maintained in the clearance or region above the tongue and the vacuum maintained in the tongue pocket are controlled at different levels. Typically, the vacuum in the pocket will be in the range from 5 $cmH_2O$ to 150 $cmH_2O$, usually 35 $cmH_2O$ to 60 $cmH_2O$, while the pressure maintained in the region above the tongue is in the range from 25 $cmH_2O$ to 50 $cmH_2O$.

Both the vacuum in the tongue pocket and the vacuum in the clearance region over the tongue will be usually drawn simultaneously (at the same time) during at least a portion of the treatment cycle, where the vacuum in each is usually provided by drawing a vacuum with a positive displacement or other vacuum pump while simultaneously bleeding in a controlled amount of air while.

INCORPORATION BY REFERENCE

All publications, patents, and patent applications mentioned in this specification are herein incorporated by reference to the same extent as if each individual publication, patent, or patent application was specifically and individually indicated to be incorporated by reference.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
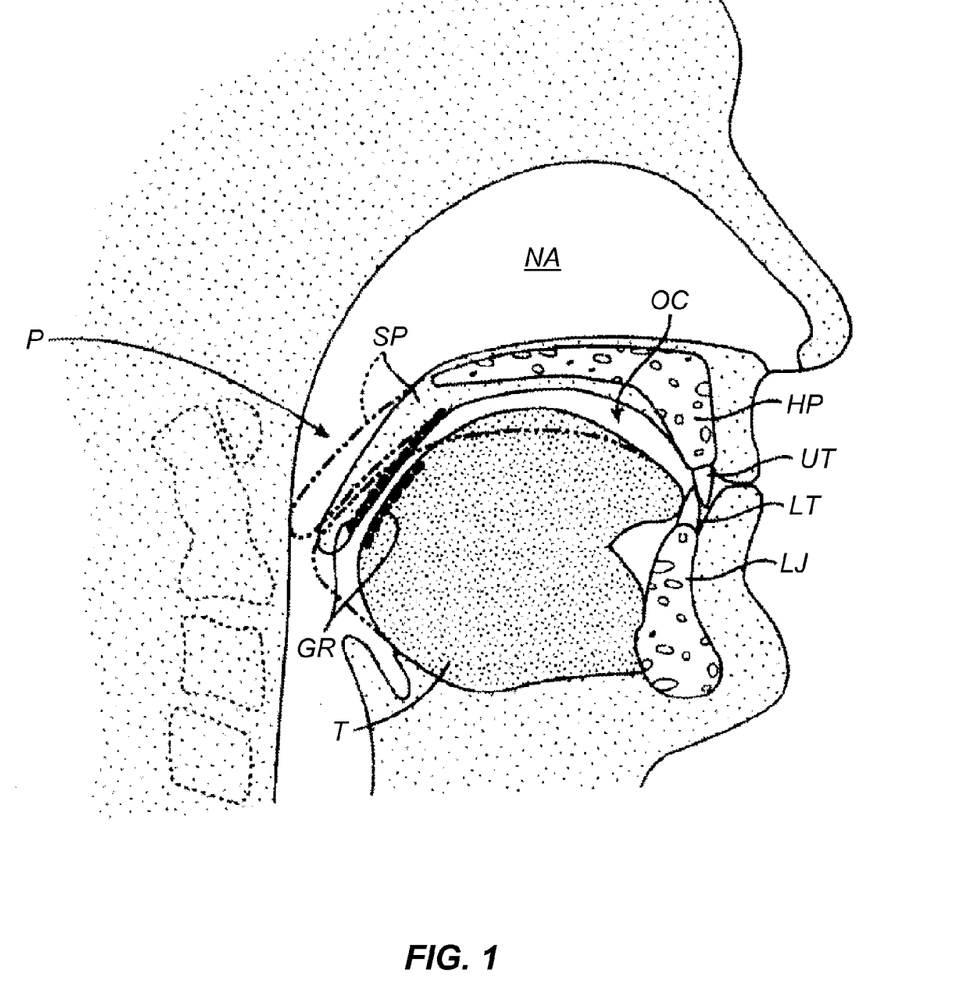
FIG. 1 illustrates the relevant anatomy of the nasal and oral cavities.

Referring to FIG. 1, the anatomy of the oral and nasal cavities relevant to obstructive sleep apnea (OSA) and the placement of the devices of the present invention will be described. The upper teeth UT of the patient are anchored in the hard palate HP, and the lower teeth LT are anchored in the lower jaw or mandible LJ. The soft palate SP extends in a rearward or posterior and inferior direction from the hard palate, and together the hard palate and soft palate divide the nasal airway NA from the oral cavity OC. The lower extent of the oral cavity is largely defined by the upper surface of the tongue T in this view, and it will be appreciated that both the soft palate SP and the tongue are mobile structures capable of movement between the positions shown in full line and broken line in FIG. 1. A nasal airway NA extends inferiorly into the pharynx P which defines the airway generally behind the soft palate SP and the tongue T. The regions on the tongue and soft palate shown with a heavy dashed line are the areas responsible for the gag reflex GR.

Obstructive sleep apnea occurs when the soft palate, the tongue or both move in a posterior direction so that they contact the rear or posterior surface of the pharynx P. The posterior motion of the soft palate and/or tongue may also reduce the size of the airway without contacting the pharynx P causing a partial blockage. The temporary blockage of the airway behind the soft palate and tongue will cause the disrupted breathing pattern characteristic of OSA and usually associated with snoring.

As used herein, "superior" refers to the direction toward the top of the oral cavity (or top of the head), "inferior" refers to the direction opposite the superior direction, "anterior" refers to the direction toward the front of the oral cavity or lips, and "posterior" refers to the direction toward the back of the oral cavity and airway, opposite the anterior direction. The terms "patency" and "airway" refer to the opening or clearing of the airway leading from the nasal cavity into the trachea located generally behind the soft palate and the rear of the tongue. To improve airway patency, the airway may be wholly or partially obstructed intermittently or temporarily for some time period over a normal sleep cycle, however, the airway will be open or partially open more than it would in the patient's untreated condition. The "upper portion of the soft palate" refers to the superior portion of the soft palate extending inferiorly from the end which connects to the hard palate to a point about ⅓-½ way toward the free inferior tip of the soft palate. The phrase "medial region" or "medial surface" of the tongue refers to a superior surface of the tongue which is spaced substantially posteriorly from the anterior tip of the patient's tongue and immediately anterior or forward of the region which initiates the gag reflex. While it may vary from patient to patient, the medial region will generally be the middle one third of the upper surface of the tongue which extends between the anterior tip of the tongue and the posterior end of the tongue (the posterior end being the location on the tongue that is furthest posterior in the oral cavity); i.e., the medial surface will usually include an area of the tongue that is at least about ⅓ of the way, more preferably at least about ½ of the way, from the anterior tip of the tongue to the posterior end of the tongue. Preferably, the medial region will include an area on the tongue posterior to the midpoint between the anterior and posterior ends of the hard palate. The phrase "clear region" refers to the space or volume above and/or posterior of the tongue which will be cleared by the methods and devices of the present invention. The clearing will usually be achieved by engaging a surface which is inclined forwardly relative to a plane of the base when the base is positioned between the upper and lower teeth and against the superior surface of the tongue, typically using a member or element which engages the tongue and which is anchored within the oral cavity so as to simultaneously advance the tongue in an anterior direction and depress the tongue in an inferior direction to open or maintain the clear region and allow the negative pressure to draw the soft palate against the tongue. The term "vacuum" and the phrase "negative pressure" each refers to a total or partial vacuum which is maintained in the clear region, typically by controlled aspiration, where the pressure is maintained primarily in the range from 5 cmH$_2$O to 150 cmH$_2$O below the local atmospheric pressure. The "occlusal plane" is the plane in which the upper and lower teeth meet when the patient bites the upper and lower teeth together.

Figure 2A:
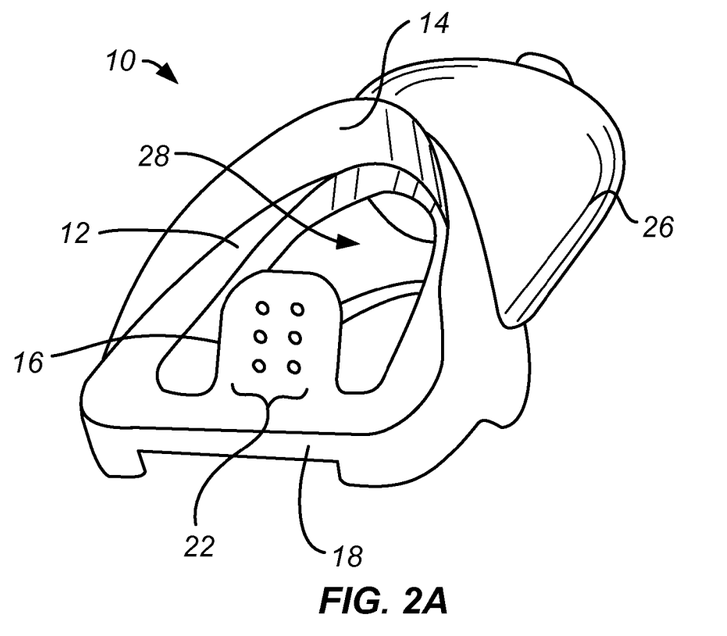
FIGS. 2A and 2B illustrate an embodiment of an oral device constructed in accordance with the principles of the present invention with FIG. 2A providing a posterior to anterior perspective and FIG. 2B showing an anterior to posterior perspective.
Figure 2B:
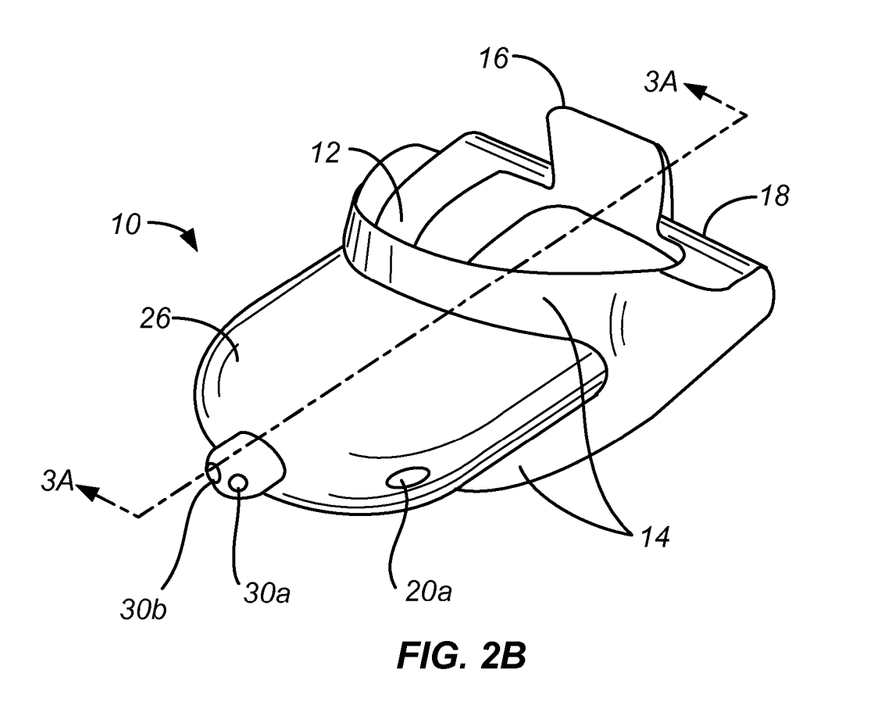

Referring now to FIGS. 2A and 2B an exemplary oral device 10 constructed in accordance with the principles of the present invention comprises a U-shaped base or anchor structure 12 having a lip seal 14 at its forward or anterior end. A tongue-engaging member 16 extends upwardly from a lateral support 18 which extends between the posterior ends of the base 12. Ports 20a and 20b (shown in FIG. 4) are provided for drawing a vacuum within the lateral support 18 which in turn can draw a partial vacuum within the patient's oral cavity through a plurality of vacuum ports 22 on a posterior surface of the tongue-engaging member 16. As described thus far, the oral device 10 is very similar to the device described in commonly owned Patent Publication No. 2012/0017917, the full disclosure of which incorporated herein by reference.

Figure 3A:
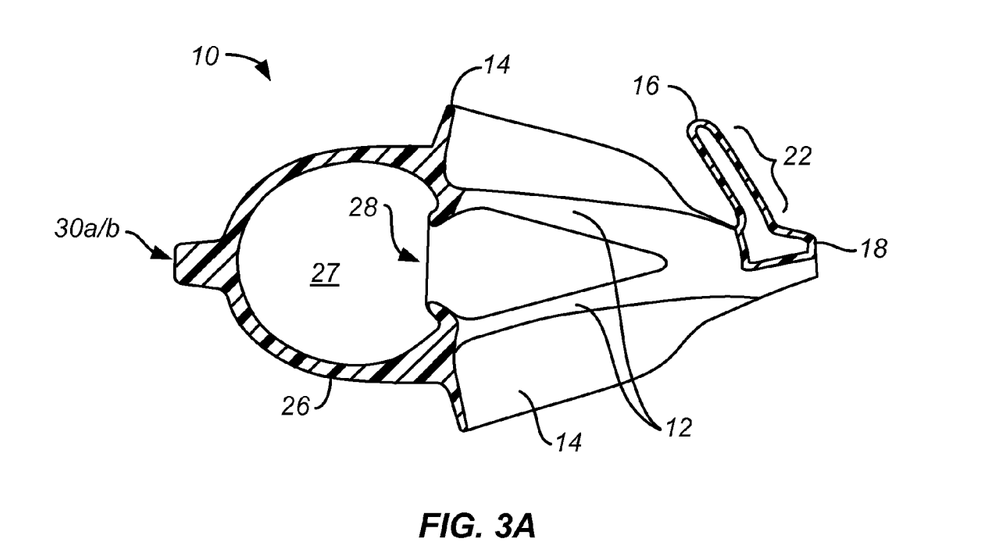
FIG. 3A is a cross-sectional view of the embodiment of FIGS. 2A and 2B taken along line 3A-3A shown in FIG. 2B.
Figure 3B:
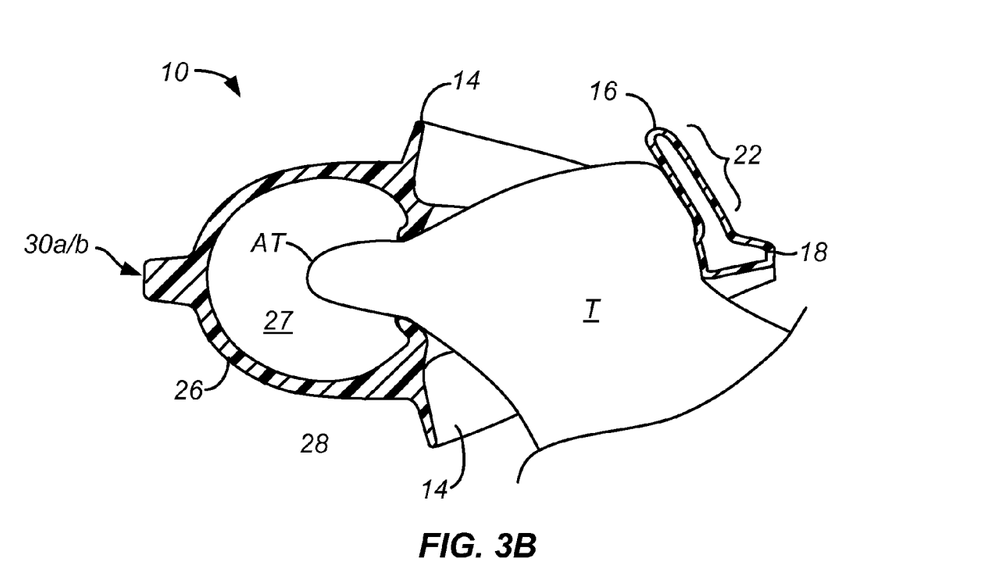
FIG. 3B is a cross-sectional view of the embodiment similar to FIG. 3A shown with a tongue being drawn into an anterior pocket and being engaged by a tongue-engaging member.

The oral devices of the present invention will further include a structural component for drawing an anterior end of the tongue forward in order to enhance clearing of the patient's airway. As shown in FIGS. 3A and 3B, the structure for advancing the tongue may comprise a dome or "tongue pocket" 26 which is secured to a forward or anterior end of the base 12 and lip seal 14. The tongue pocket 26 defines an open, interior space 27 in which a vacuum is drawn which can pull the anterior tip AT of a patient's tongue T forward through an anterior opening 28, as seen in FIG. 3B. The vacuum may be drawn through ports 30a and 30b, as described in more detail below.

Figure 4:
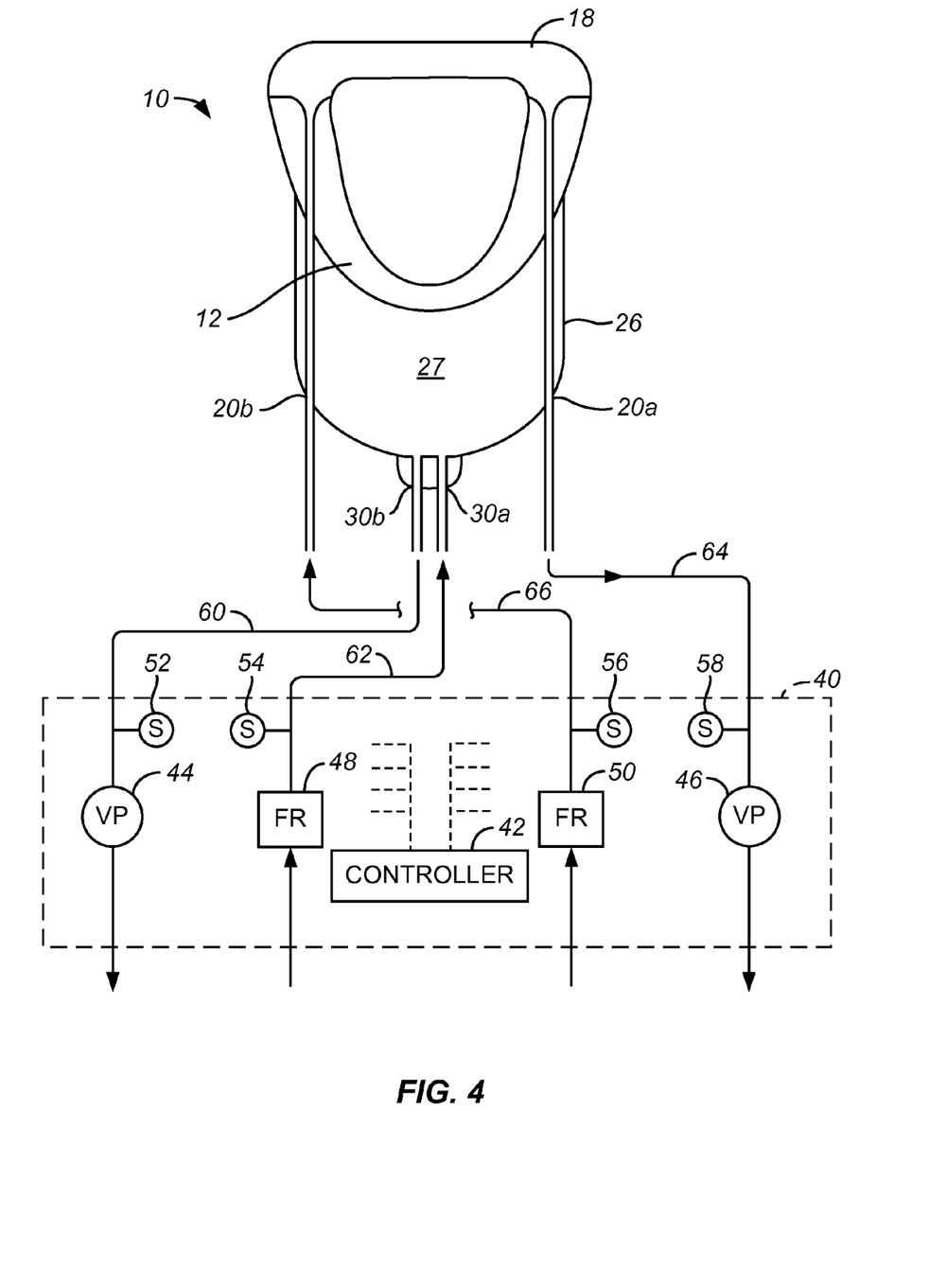
FIG. 4 is a schematic illustration of a control system or console suitable for use with the oral devices of the present invention for independently maintaining partial vacuums in the tongue pocket and in a region surrounding the tongue-engaging member.

Referring now to FIG. 4, partial vacuums may be selectively applied to the lateral support 18 and the interior 27 of the tongue pocket 26 using a console or tabletop control unit 40. The console 40 will typically include a controller 42 which will usually include a microprocessor and a dedicated interface (not shown). Conventional inputs and readouts (not illustrated) will be provided on the console 40 so that a patient or a physician can monitor operation of the system and adjust system parameters such as turning the system off and on, separately controlling and adjusting the partial vacuums drawn in the lateral support 18 (which in turn draws the vacuum in the medial and posterior regions of the patient's oral cavity) and in the interior 27 of the tongue cavity 26.

The partial vacuum in the interior 27 of the tongue pocket 26 is drawn by a vacuum pump 44 which is attached to port 30b by a tubular connector 60. The vacuum pump 44 is typically a positive displacement pump, such as a diaphragm pump, and the volume of air removed from the interior 27 can be controlled by controlling the speed of the vacuum pump 44 which in turn will control the level of vacuum within the interior, as discussed above. Typically, an air bleed is allowed to flow into the interior 27 through port 30a and a second tubular connection 62, where the flow rate is controlled by a flow restrictor 48 such as a fixed orifice, a variable flow control or pressure control valve, or the like. The vacuum level in the interior 27 of the tongue pocket 26 may be controlled, for example, by monitoring the pressure and/or flow rates of the air leaving and entering through the tubular connectors 60 and 62 using sensors 52 and 54. Typically, the pressures will be monitored and the speed of the vacuum pump 44 will be adjusted to achieve the desired vacuum level.

Similarly, the level of vacuum within the lateral support 18 (which determines the vacuum within the patient's oral cavity), will be maintained by a vacuum pump 46 which is connected to port 20a by a tubular connector 64. An air bleed stream will typically be provided through a tubular connector 66 which is connected through port 20b, where the air bleed is restricted by flow restrictor 50, which can be a fixed orifice and adjustable valve, or the like. Pressures and/or volume flow rates are monitored by sensors 56 and 58, and the controller 42 can collect the pressure and/or flow rate data in order to control the level of vacuum within the lateral support 18.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for stabilizing a soft palate in a patient's oral cavity, the patient's oral cavity having a tongue and a palate, said method comprising:
    engaging a member against a medial region of the tongue to provide a clearance between the medial region and the palate;
    applying a vacuum within the clearance to draw together the soft palate and a posterior region of the tongue; and drawing an anterior region of the tongue forward.

2. A method as in claim 1, wherein drawing the anterior region of the tongue forward comprises capturing the tongue in a tongue pocket and applying a vacuum in the pocket.

3. A method as in claim 2, wherein an anterior surface of the member is inclined forwardly relative to a plane of a base when the base is held between the upper and lower teeth and the anterior surface engages the medial region of the tongue and displaces the medial region of the tongue in an anterior direction relative to the soft palate.

4. A method as in claim 3, wherein the vacuum is applied to the clearance through ports disposed over a posterior surface of the member.

5. A method as in claim 2, wherein the vacuum in the clearance and the vacuum in the tongue pocket are maintained at different levels.

6. A method as in claim 2, wherein the vacuum in the clearance is less than the vacuum in the tongue pocket.

7. A method as in claim 2, wherein the vacuum in the clearance is in the range from 25 $cmH_2O$ to 50 $cmH_2O$ and the vacuum in the tongue pocket is in the range from 35 $cmH_2O$ to 60 $cmH_2O$.

8. A method as in claim 2, wherein applying the vacuum in the clearance comprises continuously drawing a vacuum while simultaneously bleeding in a controlled amount of air to maintain a desired partial vacuum.

9. A method as in claim 2, wherein applying the vacuum in the tongue pocket comprises continuously drawing a vacuum while simultaneously bleeding in a controlled amount of air to maintain a desired partial vacuum.

10. A method as in claim 2, wherein the vacuum in the clearance draws the soft palate against the posterior surface of the member.

11. A method as in claim 2, wherein the soft palate remains spaced-apart from the posterior surface of the member while the vacuum in the clearance is being applied.

12. An oral device for temporary placement in a patient's oral cavity, said device comprising:
    a base adapted to be held between the patient's upper and lower teeth, the base defining an anterior opening which is adapted to allow the patient's tongue to pass therethrough;
    a tongue-engaging member coupled to the base and disposed to engage a medial region of the tongue when the base is positioned between the patient's teeth, the tongue-engaging member comprising one or more ports;
    and a tongue pocket coupled to the base and having an interior disposed to receive an anterior region of the patient's tongue when the tongue passes through the anterior opening;
    wherein the one or more ports are adapted to be connected to a vacuum source to apply a partial vacuum between the tongue-engaging member and a roof of the mouth.

13. An oral device as in claim 12, wherein the base comprises an upper plate for receiving the upper teeth and a lower plate for receiving the lower teeth, wherein the upper and lower plates diverge in the anterior direction so that the base holds the patient's upper teeth and lower teeth apart to provide the anterior opening therebetween.

14. An oral device as in claim 13, wherein the upper and lower plates each comprise a U-shaped bite plate configured to be positioned against full dentition.

15. An oral device as in claim 14, wherein the tongue-engaging member has an anterior surface and a posterior surface where the anterior surface is inclined forwardly relative to a plane of the base and is disposed to engage a medial region of the tongue when the base is held between the patient's upper and lower teeth.

16. An oral device as in claim 15, wherein the tongue-engaging member has an integral plenum connectable to the vacuum source with at least one port disposed on a posterior surface of the tongue-engaging member and open to the integral plenum.

17. An oral device as in claim 15, wherein the tongue-engaging member has a plurality of ports distributed over the posterior surface thereof.

18. An oral device as in claim 15, wherein the anterior surface and the posterior surface of the tongue-engaging member are inclined forwardly at an angle in the range from 45 degrees to 60 degrees relative to a plane of the base when positioned between the upper and lower teeth.

19. An oral device as in claim 15, wherein the anterior surface of the tongue-engaging member is generally parallel to the posterior surface of the tongue-engaging member.

20. An oral device as in claim 13, wherein the base further comprises a lip seal extending above the upper plate and below the lower plate to seal the patient's oral cavity when the base is held between the patient's teeth.

21. An oral device as in claim 13, wherein the tongue pocket extends in an anterior direction from the lip seal.

22. An oral device as in claim 12, wherein the tongue pocket is adapted to be connected to a vacuum source to apply a partial vacuum in an interior of the tongue pocket to draw the patient's tongue in an anterior direction.

23. An oral device as in claim 22, further comprising a vacuum source which is connectable to the tongue pocket and the tongue-engaging member.

24. An oral device as in claim 23, wherein the vacuum source comprises a single vacuum source and wherein the single vacuum source is separately connected to and adjustable for each of the tongue pocket and the tongue-engaging member.

25. An oral device as in claim 24, wherein the vacuum source is adapted to draw a vacuum in the range from 35 $cmH_2O$ to 60 $cmH_2O$ in the tongue pocket and a vacuum in the range from 25 $cmH_2O$ to 50 $cmH_2O$ through the tongue-engaging member.

26. An oral device as in claim 24, wherein the tongue pocket has a vacuum port and a bleed port to allow a continuous air flow through the tongue pocket while maintaining a partial vacuum.

27. An oral device as in claim 26, wherein the tongue-engaging member has a vacuum port and a bleed port to allow a continuous air flow therethrough while maintaining a partial vacuum in the oral cavity.

28. An oral device as in claim 27, further comprising a vacuum source which is connectable to the tongue pocket and to the tongue-engaging member, wherein the vacuum source is connectable to the vacuum port and the bleed port of the tongue pocket and the vacuum port and the bleed port of the tongue-engaging member to provide a continuous air flow to each of the tongue pocket and the tongue-engaging member while maintaining a partial vacuum.

* * * * *

UNITED STATES PATENT AND TRADEMARK OFFICE
CERTIFICATE OF CORRECTION

PATENT NO.        : 8,387,620 B1
APPLICATION NO.   : 13/593137
DATED             : March 5, 2013
INVENTOR(S)       : Matthias Vaska et al.

Page 1 of 1

It is certified that error appears in the above-identified patent and that said Letters Patent is hereby corrected as shown below:

On the Title Page, Item (75)

Replace inventors name 'Michael C. Hozbaur' with --Michael C. Holzbaur--.

Signed and Sealed this
Tenth Day of December, 2013

Margaret A. Focarino
*Commissioner for Patents of the United States Patent and Trademark Office*